(12) United States Patent
Alboum et al.

(10) Patent No.: US 6,328,952 B1
(45) Date of Patent: Dec. 11, 2001

(54) AIR FRESHENER DEVICE

(75) Inventors: Howard Alboum, East Orange; John Williams, Bayonne; Ruggiero Abbatemarco, Edison, all of NJ (US)

(73) Assignee: Scientific Mfg. Co., Inc., East Orange, NJ (US)

( * ) Notice: Subject to any disclaimer, the term of this patent is extended or adjusted under 35 U.S.C. 154(b) by 0 days.

(21) Appl. No.: 09/569,691

(22) Filed: May 15, 2000

Related U.S. Application Data (60) Provisional application No. 60/134,237, filed on May 14, 1999.

(51) Int. Cl.[7] ................ A61L 9/00; A61L 9/01
(52) U.S. Cl. .......................... 424/76.1; 424/76.2
(58) Field of Search ................ 424/76.1, 76.2

(56) References Cited

U.S. PATENT DOCUMENTS

| | | | |
|---|---|---|---|
| D. 345,787 | * 4/1994 | Martin | D23/366 |
| 4,155,500 | 5/1979 | Dutcher . | |
| 4,166,568 | 9/1979 | Webinger . | |
| 4,208,012 | * 6/1980 | Dutcher | 239/57 |
| 4,279,373 | 7/1981 | Montealbare . | |
| 4,712,737 | 12/1987 | Hecking . | |
| 5,938,111 | * 8/1999 | Grigsby | 229/155 |

* cited by examiner

*Primary Examiner*—Thurman K. Page
*Assistant Examiner*—Liliana Di Nola-Baron
(74) *Attorney, Agent, or Firm*—Weingram & Associates. P.C

(57) ABSTRACT

A dispenser for a volatile aromatic substance is provided which includes a closed container formed from a single blank of folded sheet material in which the aromatic substance is deposited. The blank is folded to form a plurality of coacting interior and exterior walls, one of the walls having a tab form which is broken along a line of weakness to expose at least one vent passage in an underlying interior wall through which the vapors of the aromatic substance may pass. The tab form is hingedly connected to the blank so that it will not be removed therefrom and in one embodiment, coacts with a vent passage so that the tab form is displaced from underlying interior walls to modulate the circulation of vapors flowing from the vent passages. A hermetic coating is provided to preserve the shelf life of the container, including the aromatic substance deposited therein.

6 Claims, 9 Drawing Sheets

AIR FRESHENER DEVICE

This application claims benefit of Provisional Application Serial No. 60/134,237 filed May 14, 1999.

BACKGROUND OF THE INVENTION

The present invention relates to air fresheners constructed as as a box or carton which is breached to permit a scent to emanate from the carton and in particular, to those devices constructed to modulate the dispensing of the scent.

Air fresheners are widely used in the market today. They have great popularity and come in various sizes, shapes and different dispensing systems. Most of the known air freshener systems are manufactured of plastics and other materials that have several components which require time consuming and costly measures in order to manufacture and assemble the desired product.

Some types of air fresheners use a gel containing a scent which is heated by plugging the device into a wall socket. The heat from a coil tends to produce evaporation at a controlled rate. There may be various dampers, like a fireplace damper, which control the airflow out from the scented material.

There are also liquid devices which have a reservoir that is connected to an enlarged dispensing wick on the bottom of the device, and various features at a top thereof to allow for modulation of the dispersed scent.

Known air freshening devices include those disclosed in U.S. Pat. Nos. 4,155,500 to Dutcher, U.S. Pat. No. 4,166,565 to Webinger, U.S. Pat. No. 4,279,373 to Montealegre, and U.S. Pat. No. 4,712,737 to Hecking.

Many of these known devices are constructed in containers that have to be discarded when the scent has been exhausted. The container controls and seals the scented product while it is on the shelf, after which the container is deployed for use and then destroyed.

SUMMARY OF THE INVENTION

The present invention provides an air freshener device which is self-contained in its own shipping container which becomes the dispenser when used.

The shipping container of the present invention allows for sealing the device effectively during shipping or storage to prevent deterioration and to retain odors from the air freshening scent which could be overpowering if released in an overly concentrated form.

The present invention includes a box or container assembled from a single blank which is scored, cut and folded to form the container for the air freshening receptacle in which is disposed a blotter or other type of absorbent material that has been saturated with a freshening scent substance. A portion of the container is constructed and arranged as a modulating member to permit release of the scent from the container and thereafter regulate the intensity of the scent being dispensed.

OBJECTS OF THE PRESENT INVENTION

It is an object of the present invention to provide an air freshener device which is self-contained and the container therefor is manufactured for dispensing the air freshener product.

It is another object of the present invention to construct a container for the device which is made from a single blank, the blank being scored, cut and folded to be assembled into the container for the air freshening receptacle.

It is another object of the present invention to provide an air freshener device wherein the container is assembled to provide the blotter or another type of absorbent material that has been saturated with a freshening substance to emanate from the container.

It is another object of the present invention to provide an air freshener device constructed with a shipping container having a MYLAR® seal extending around the container to prevent deterioration of the packaging for the container and the unintentional release of the scent which can be overpowering in concentrated form.

It is another object of the present invention to provide a box for the air freshener device to include front, back, side panels and an additional front panel portion which is constructed and arranged to wrap around the box and a select portion of the side panels.

It is another object of the present invention to provide a box for the air freshener device having a panel position which extends or wraps around a front of the box to cover a plurality of scent dispensing apertures in the front panel and the side panel when the box is assembled to regulate scent flow.

It is another object of the present invention to provide a box for an air freshener device constructed from a blank having an outer surface with a MYLAR® coating to act as a fluid barrier to prevent deterioration of the contents of the box and prevent the scent from escaping from the closed box.

It is another object of the present invention to provide a box for an air freshener device having scent radiating apertures of a particular construction and arrangement such that orientation of the box facilitates the direction from which the freshening scent escapes from the box.

It is another object of the present invention to provide a box for an air freshener device having a perforated front cover portion adapted for removal for releasing the freshening scent and having a portion thereof remaining attached to the box so that it can be discarded with the box when the scent is exhausted.

BRIEF DESCRIPTION OF THE DRAWINGS

For a more complete understanding of the present invention, reference may be had to the following detailed description of the preferred embodiments of the invention taken in conjunction with the drawings, of which.

DETAILED DESCRIPTION OF THE PREFERRED EMBODIMENTS

Figure 1:
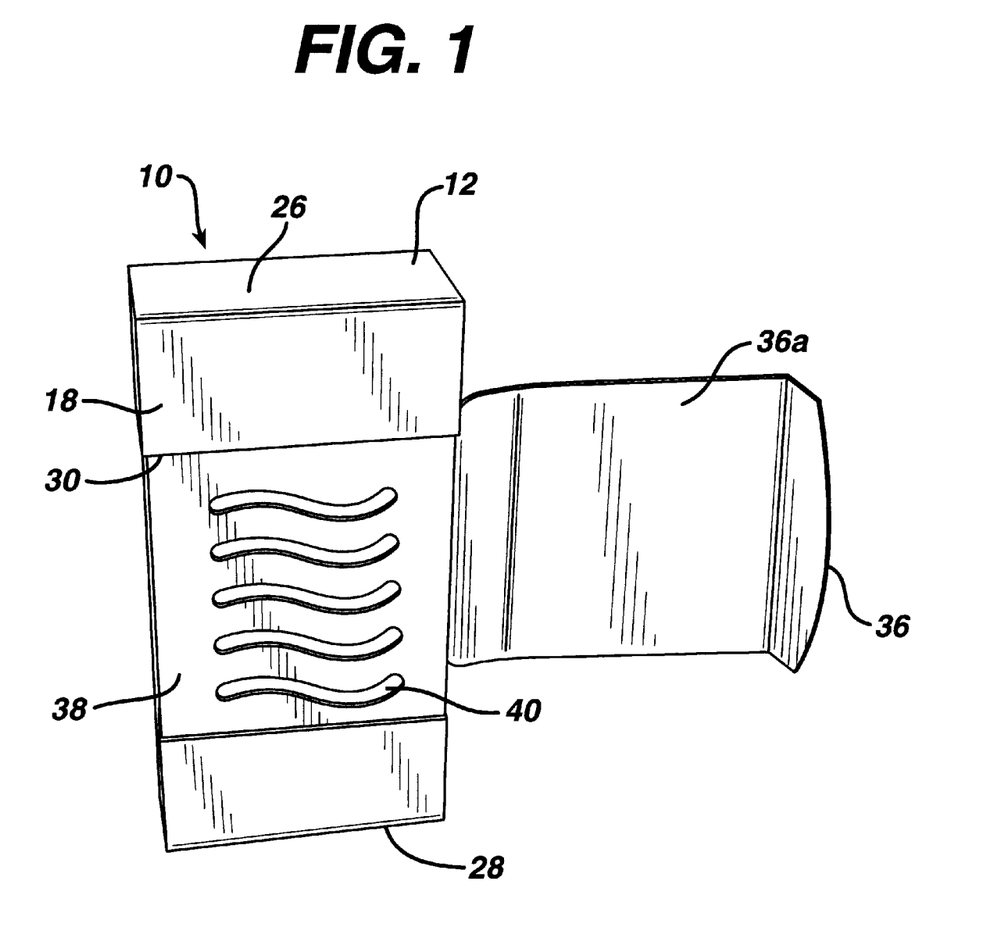
FIG. 1 is a view of an air freshener device according to the present invention.
Figure 2:
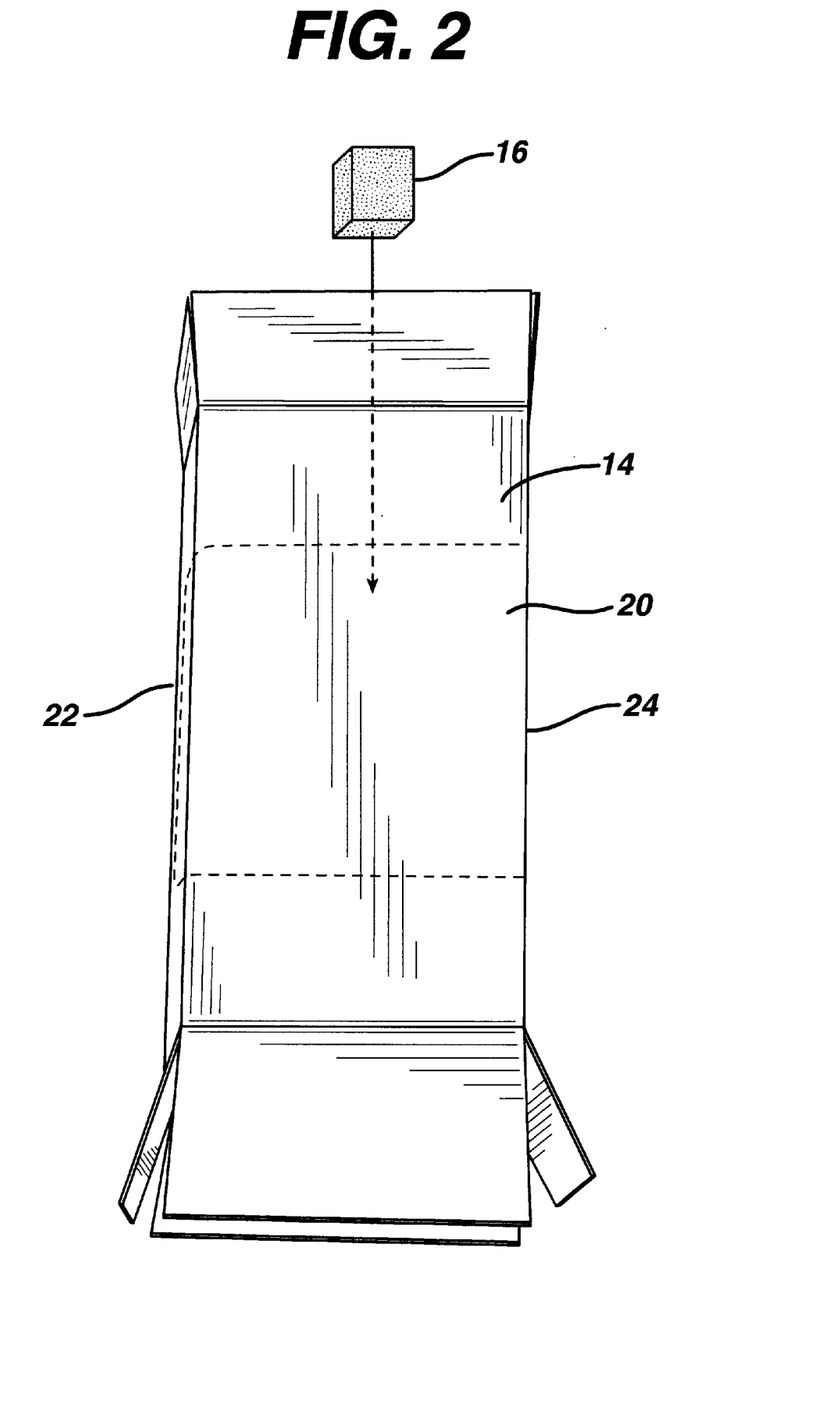
FIG. 2 is a back view of a blank being assembled to form a container for the device of the present invention.

Referring to FIGS. 1–2, an air freshener device of the present invention shown generally at 10. The device 10 is constructed of a closed box or container 12. The container 12 is formed from a blank 14 of a sheet of material constructed to form the container 12. A description regarding the construction of the container from the sheet material of the blank 14 will be discussed below. A volatile aromatic substance 16, which can be of any number of constructions and arrangements, is deposited within the closed container 12. The aromatic substance can also be in a liquid form deposited on an absorbent pad or other supporting structure.

As shown in the FIGS. 1–2 referred to, the container 12 is also provided with a top 26 and a bottom 28.

In general, and as shown in FIG. 1, when a removable area of the container is displaced therefrom, at least one and preferably a plurality of vent passages 40 are exposed through which vapors from the aromatic substance are ventilated.

Figure 3:
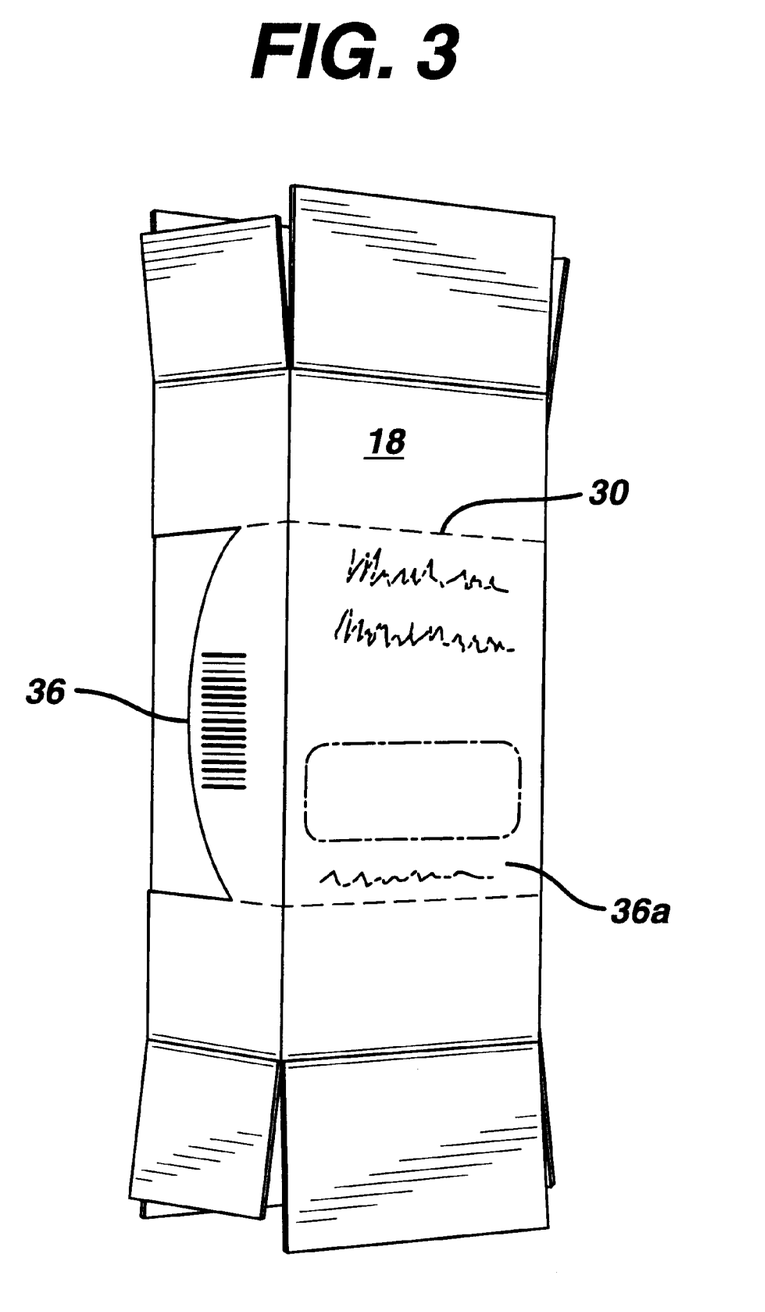
FIG. 3 is a front perspective view of the blank for the device prior to final assembly showing a scored displaceable portion at the front panel.
Figure 4:
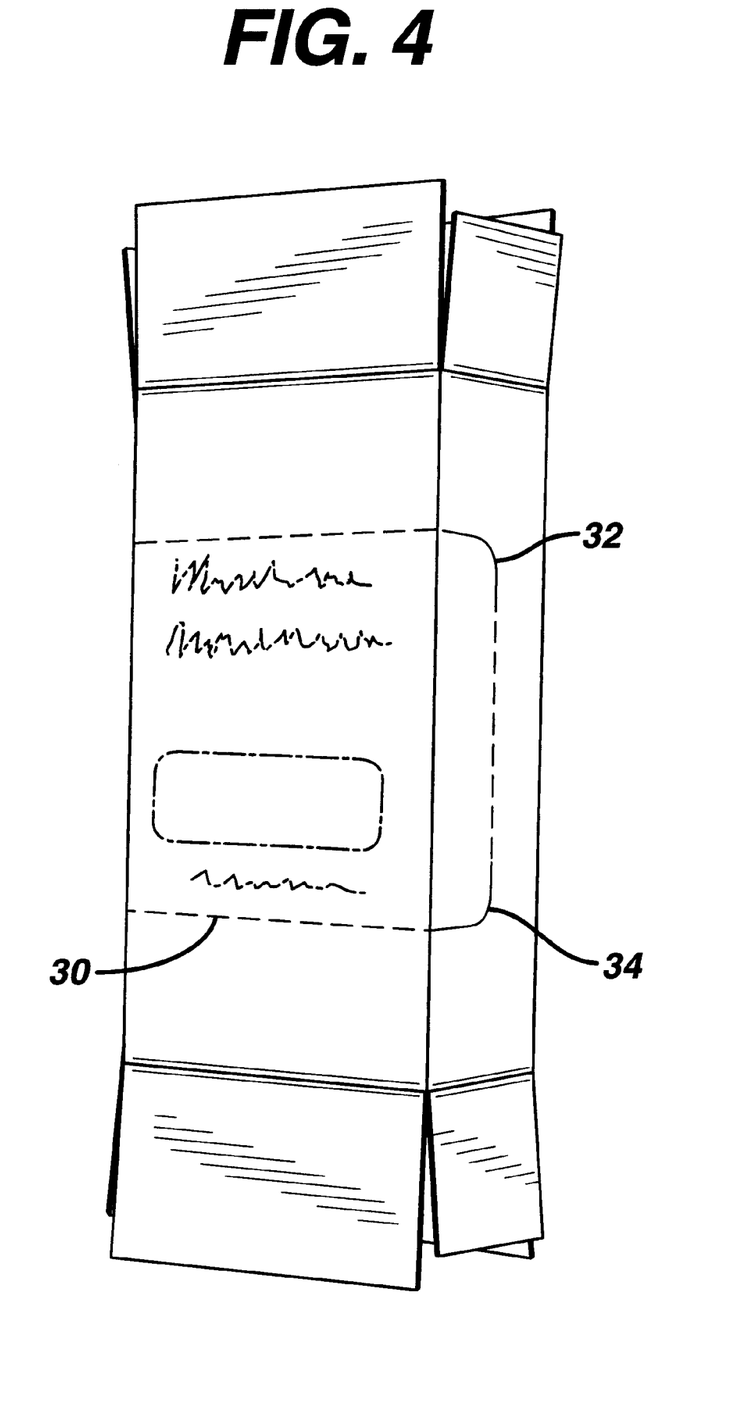
FIG. 4 is another front perspective view of the blank for the device prior to final assembly showing the scored displaceable portion at the front panel.
Figure 5:
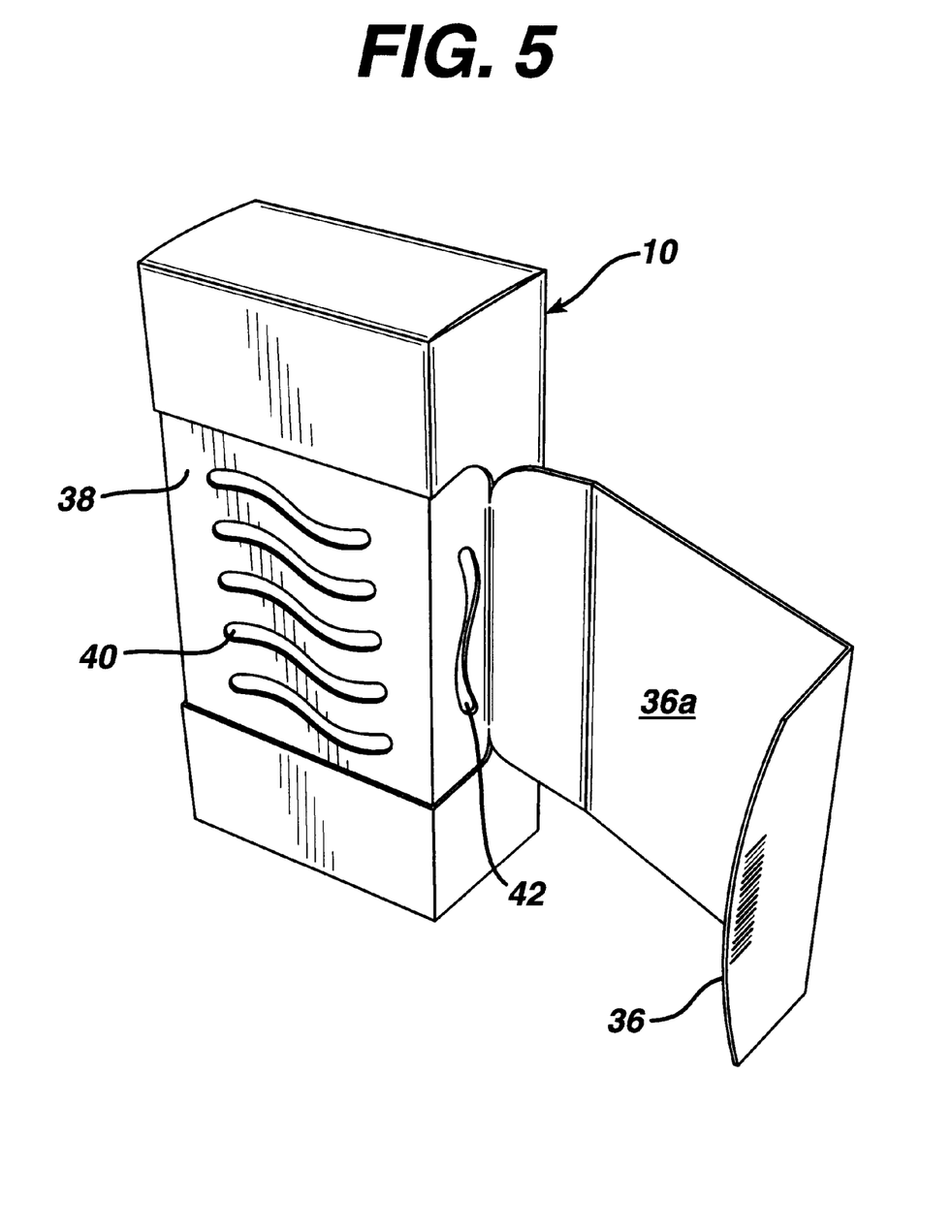
FIG. 5 is a top perspective side view of a removable area panel portion displaced from the container to disclose a vent panel of the device.
Figure 6:
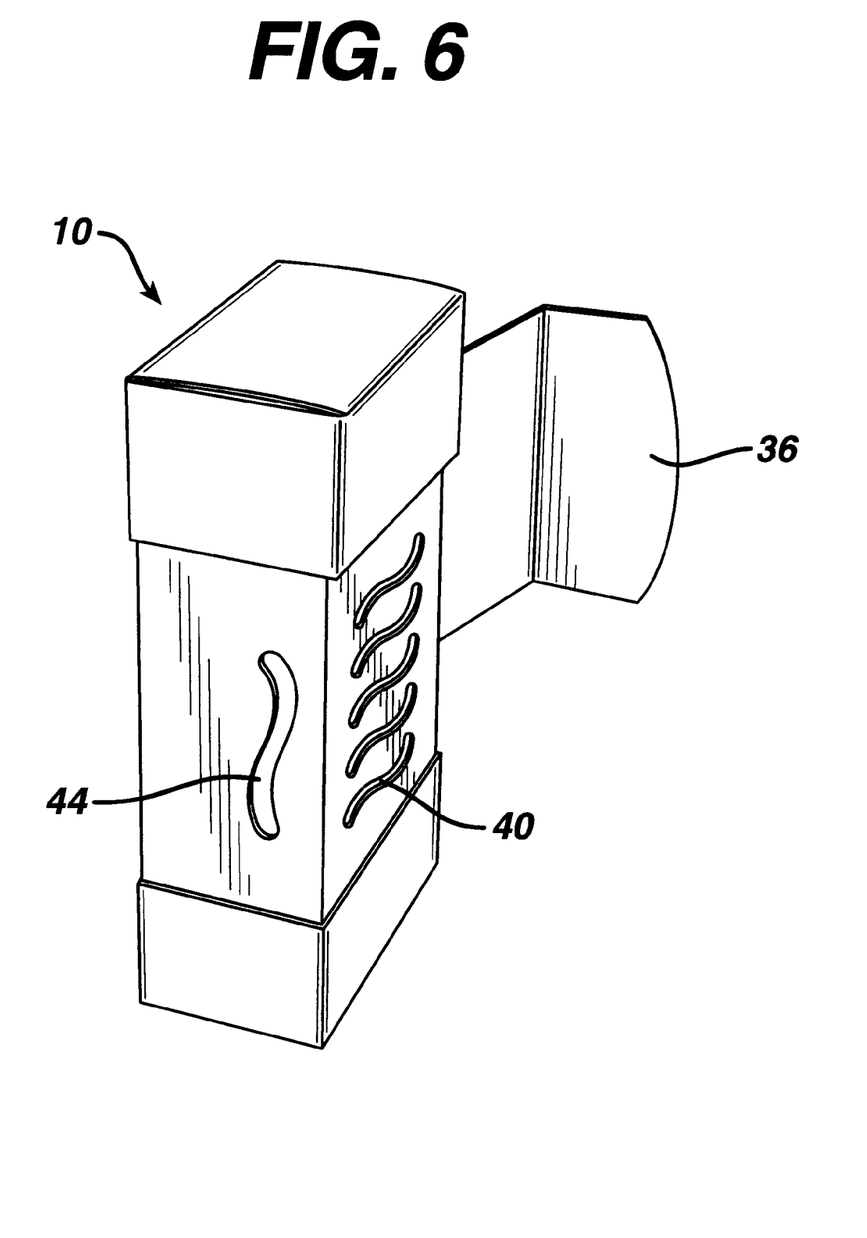
FIG. 6 is a top perspective view of the device taken from an opposite side to that shown in FIG. 5.

Referring also to FIGS. 3 and 4, exterior front and side walls of the container 12 are provided with scoring 30 to define a line of weakness extending across the exterior front wall and side walls. The scoring 30 permits a portion of the container 12 to be displaced therefrom so that the vent passages 40 are exposed. As shown in FIG. 3 and 4, surface indicia printed on the container 12 can be used to designate the source or origin of the product, as well as the consumer barcode information.

Referring also to FIG. 4, the scoring 30 continues to define a tab form 36 which is grippable to displace the tab area 36a away from the container 12. Displacement of the tab form 36 from the container 12 also exposes at least one other vent passage 42, 44 at opposed sides of the container 12. This arrangement of vent passages 42, 44 provides for increased venting of the aromatic substance as those situations warrant.

Hinges 32, 34 permit the tab area 36a to be hingedly moved away from the container without being separated therefrom.

Figure 7:
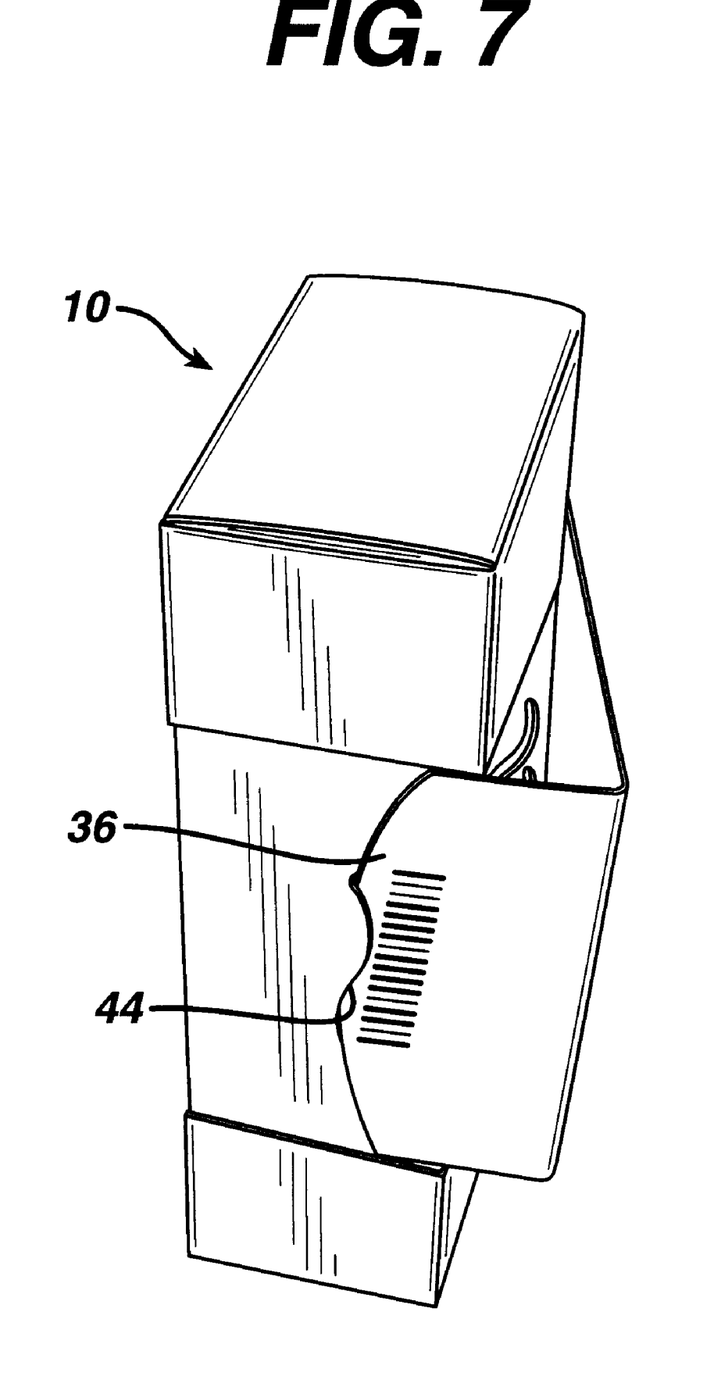
FIG. 7 is a perspective view from a side of the device showing the removable panel portion retained in place to regulate the flow of a scent to be dispersed.
Figure 8:
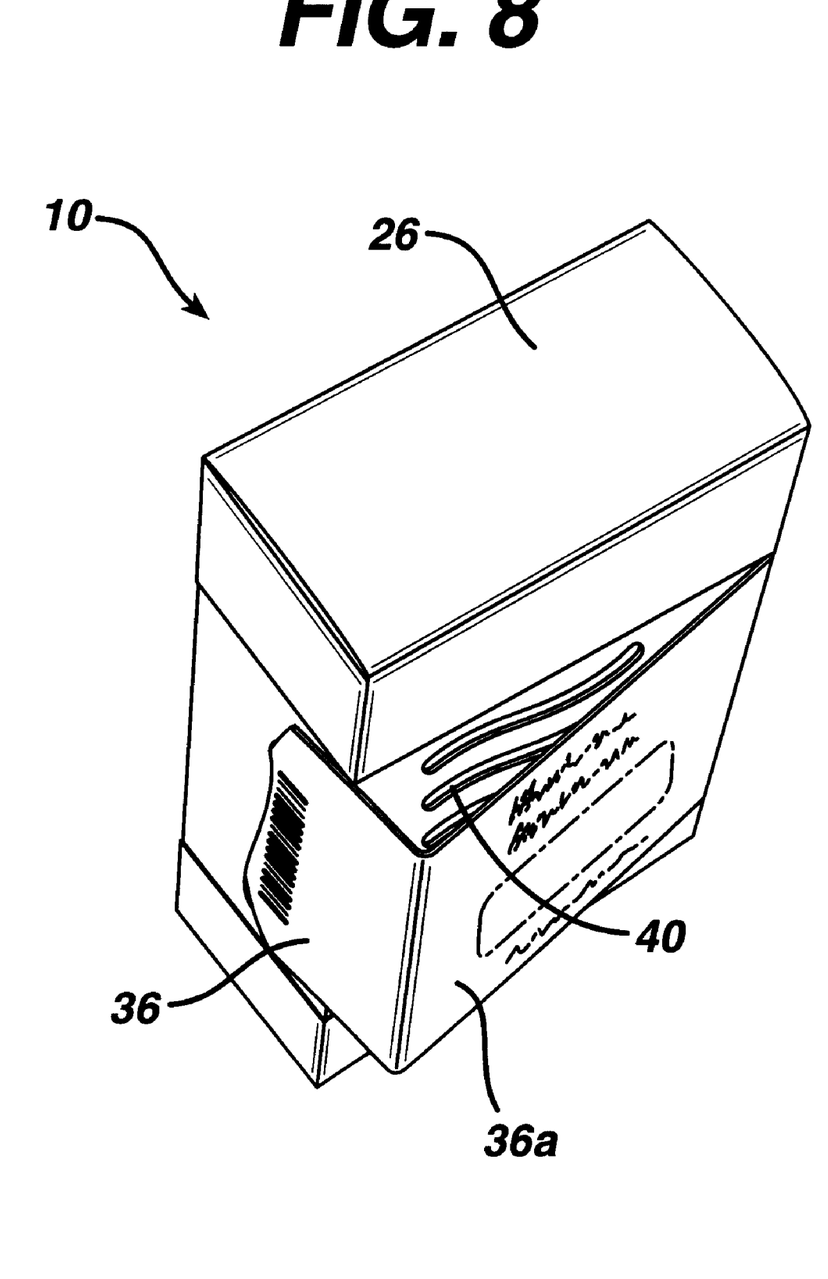
FIG. 8 is a top perspective view of the device of the present invention with the cover adjusted and retained to regulate the dispersing of an aromatic scent.

In FIG. 7, the tab form 36 has been inserted in the side vent passage of 44 of the container 12 to displace the tab area 36a from the vent passages 40 at the front container 12. With this manner of construction and arrangement of the tab form 36, venting of the aromatic substance 16 is restricted and deflected so that the vapors are not introduced as densely into the surrounding environment.

Figure 9:
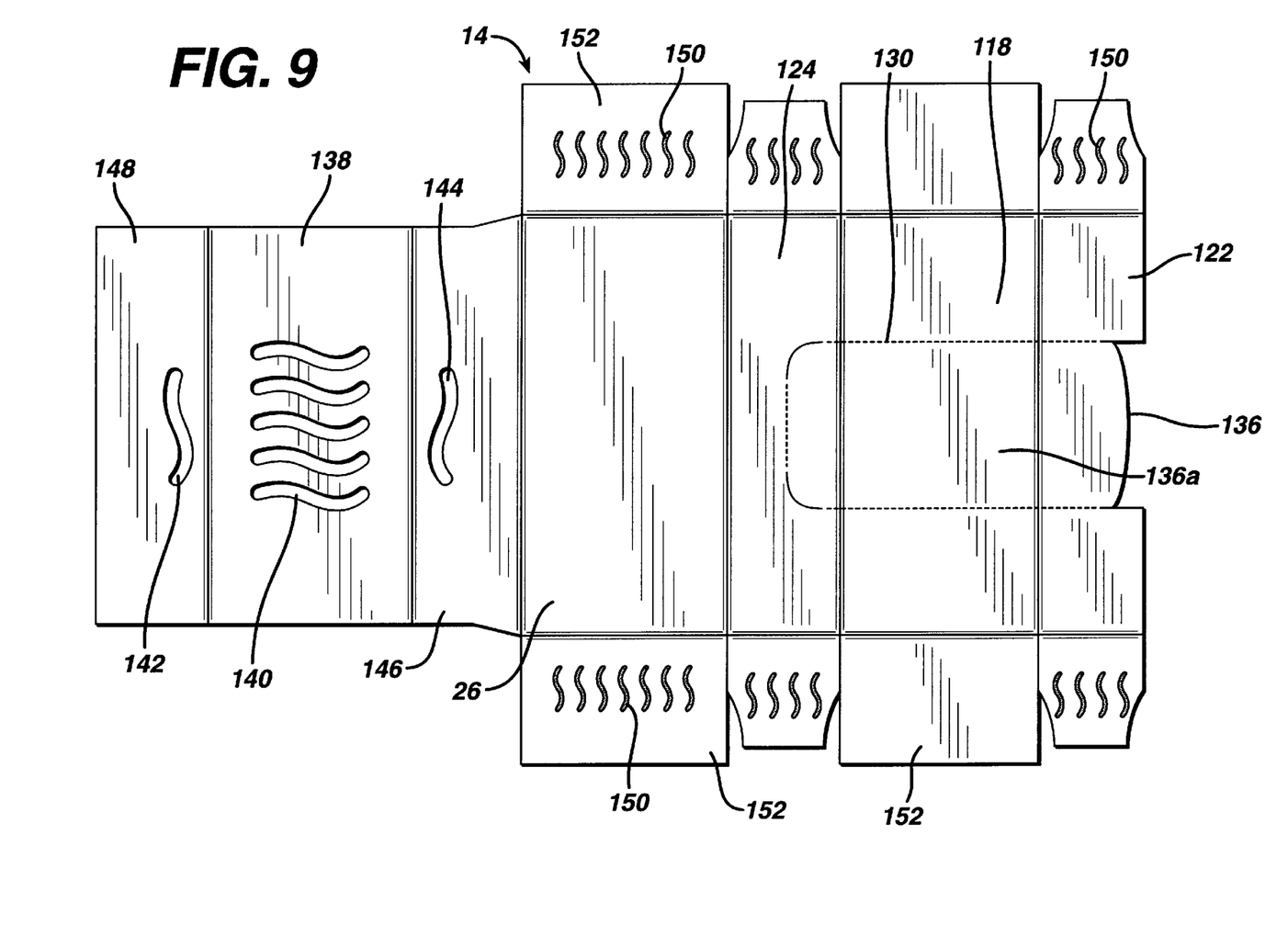
FIG. 9 is a plan view of a sheet material used to form a blank rom which the air freshener device is constructed.

Referring to FIG. 9, the blank 14 is shown from which is constructed the air freshener device 10 of the present invention. The blank 14 is formed from cardboard 14 or other paper product and coated with, for example, MYLAR®. The aromatic substance 16 is disposed within the assembled container 12 before the container is sealed closed.

The blank 14 includes an internal wall 138 and internal side walls 146, 148, and external front wall 118 and external side walls 122, 124 which wrap around the internal front and side walls. The internal front wall 138 is closely congruent with the external front wall 118 for folding of the external front wall around the internal front wall. The blank 14 from which the container 12 is made has a MYLAR® coating which acts as a fluid barrier and hermetic seal to prevent the aromatic substance 16 from deteriorating and vapors from emanating from the closed container when not in use. This preserves the shelf life of the unused container. The MYLAR® coating of the blank 14 restricts vapors from escaping from the container only through the vent passages 140, 142, 144, which are formed to provide directional effect by positioning of the container 12 and the tab form 136.

The front external wall 118 and side walls 122, 124 are scored with perforations 130 to provide a line of weakness in the blank 14. The tab area 136 is removed by lifting same which is lightly glued to the underlying interior side wall 146. Once the tab 136 is lifted, the perforations 130 will fragment or fracture and allow the tab form 136 and area 136a to be peeled back along the perforations 130 to disclose the vent passages 140, 142, 144. The tab 136 can be inserted into the vent passage 144 to act as a modulating member to adjust the amount of vapor that will radiate from the vent passages.

The aromatic substance 16 contains air freshening material, such as an oil or a perfume, and is placed into the container 12 which is made from the one piece blank 14. It may contain a wick and is airtight. There may also be plastic wrap (not shown) around the container 12. A die (not shown) is used to form the lines of weakness and perforations 130 in the blank 14.

The MYLAR® coating produces an almost hermetic seal. To open the container 12 to allow the air freshener to be used, the tab 36 is pulled so the tab 36 is removed along the perforations 30. This allows the scent to evaporate and radiate out through the vent passages 140, 142, 144 into the air. The device 10 is sold as a complete package, with printing fields for indicia located at various regions along the exterior of the container 12.

Adhesive 150 is used to secure the blank 14 into its folded arrangement as the container 12 such as along the flaps 152.

It will be understood that the embodiments described herein are merely exemplary and that a person skilled in the art may make many variations and modifications without departing from the spirit and scope of the invention. All such variations and modifications are intended to be included in the scope of the invention as described herein and called for in the appended claims.

What is claimed is:

1. A dispenser for a volatile aromatic substance comprising:

a closed container made from a single blank of folded sheet, material having a top and bottom side;

a layer of hermetic material coating at least one of the top and bottom sides;

a quantity of a volatile aromatic substance deposited on an absorbant pad within the closed container;

the closed container comprising:

external front and rear walls, external opposite side walls attached between said external front and rear walls, top and bottom closing flaps to seal the container, an internal front and side walls, said internal front and side walls underlying adjacent external front and side walls, each of said internal side walls having at least one vent passage, said internal front wall having a plurality of vent passages, each of said internal front and side walls being dimensioned to allow the adjacent external front and side walls to fold around said internal front and side walls, scoring on the external side walls and external front wall to define a partially removable external front and side wall flap area that folds around and covers the vent passages in the internal front wall and internal side walls in a closed position, one end of said flap area having a hinged foldable connection to one external side wall, the other end of said flap area having a tab form at the other external side wall, said tab form facilitating separation of the partially removable area from the external side walls and external front wall to expose the vent passages on the underlying internal side walls and internal front wall, said scoring allowing the partially removable area to be displaced from the other external side wall and the internal front wall without removal from the container, said tab form coacting with one of the vent passages to enable the partially removable area to be held in position displaced from the vent passages in the internal front wall to partially block circulation from the vent passages in the internal front wall.

2. A dispenser for a volatile aromatic substance comprising;

a closed container made from a single blank of folded sheet material having top and bottom surfaces;

a quantity of volatile aromatic substance within the closed container, the closed container comprising:

external front and rear walls, external opposite side walls attached between said external front and rear walls, top and bottom closing flaps to seal the container, an internal front wall and internal side walls, said internal front and side walls underlying adjacent external front and side walls, at least one of said internal side walls having at least one vent passage, said internal front wall having at least one vent passage, said one internal side wall and internal front wall being dimensioned to allow the adjacent external side and external front walls to fold around said one internal side wall and internal front wall, said external side wall adjacent said one internal side wall ending in a tab form, scoring on said external side wall adjacent said one internal side wall and on the external front wall to define a partially removable external wall flap area that folds around and covers the vent passage in the internal front wall and internal side wall in a closed position, said tab form being positioned at one end of said removable area of said external side wall adjacent said one underlying internal side wall to facilitate separation of the partially removable area from said external side wall and external front wall to expose the vent passages at said internal side wall and internal front wall, said scoring including a hinged foldable connection portion on the other of said external side walls to allow the partially removable area to be displaced from the internal front wall and one internal side wall without removal from the container to allow circulation of said volatile material from said container through said vent passages.

3. The dispenser according to claim 2, wherein said internal front wall includes a plurality of vent passages.

4. The device according to claim 2, wherein said tab form is adapted to coact with one of the vent passages to enable the partially removable area to be held in position displaced from the vent passages in the internal front wall to partially block circulation from the vent passages in the internal front wall.

5. The device according to claim 2, further comprising:

a layer of hermetic material coating at least one of the top and bottom surfaces of said sheet material of said blank.

6. The device of claim 4 wherein said tab form is insertable into said vent passage in said one internal side wall.

* * * * *